(12) United States Patent
Liu et al.

(10) Patent No.: US 11,813,483 B2
(45) Date of Patent: Nov. 14, 2023

(54) NEUTRON CAPTURE THERAPY SYSTEM

(71) Applicant: NEUBORON MEDTECH LTD., Jiangsu (CN)

(72) Inventors: Yuanhao Liu, Jiangsu (CN); Weilin Chen, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 741 days.

(21) Appl. No.: 16/839,188

(22) Filed: Apr. 3, 2020

(65) Prior Publication Data
US 2020/0246639 A1  Aug. 6, 2020

Related U.S. Application Data

(63) Continuation of application No. PCT/CN2018/100963, filed on Aug. 17, 2018.

(30) Foreign Application Priority Data

Dec. 15, 2017  (CN) .......................... 201711348389.9
Dec. 15, 2017  (CN) .......................... 201711350436.3
(Continued)

(51) Int. Cl.
*A61N 5/10* (2006.01)
(52) U.S. Cl.
CPC ...... *A61N 5/1081* (2013.01); *A61N 2005/109* (2013.01); *A61N 2005/1094* (2013.01)
(58) Field of Classification Search
CPC ...... A61N 2005/109; A61N 2005/1094; A61N 5/1081; A61N 5/1078; A61N 5/10; A61N 2005/1095
See application file for complete search history.

(56) References Cited

U.S. PATENT DOCUMENTS 3,715,597 A  2/1973  Hofmann et al.

FOREIGN PATENT DOCUMENTS

CN  104429168 A  3/2015
CN  106474633 A  3/2017
(Continued)

OTHER PUBLICATIONS

State Intellectual Property Office of the P.R. China (ISR/CN), "International Search Report for PCT/CN2018/100963", China, dated Nov. 9, 2018.

*Primary Examiner* — Christine H Matthews
(74) *Attorney, Agent, or Firm* — Locke Lord LLP; Tim Tingkang Xia, Esq.

(57) ABSTRACT

The present disclosure provides a neutron capture therapy system, including a neutron generator to generate neutrons after irradiation by charged particles, and a beam shaping assembly includes a moderator and a reflector surrounding the moderator. A vacuum tube connected to the accelerator is provided at an accommodating portion. The vacuum tube transmits the charged particles accelerated by the accelerator to the neutron generator to generate neutrons. The neutron generator moves between a first position and a second position, at the first position, the neutron generator react with the charged particle beam to generate neutrons, at the second position, the neutron generator falls off the beam shaping assembly. The vacuum tube is detached to make the neutron generator fall off the beam shaping assembly, to reduce direct contact of a worker with the neutron generator after nuclear reactions, thereby reducing radioactive hazards for workers.

20 Claims, 10 Drawing Sheets

(30)  Foreign Application Priority Data

Dec. 15, 2017 (CN) .......................... 201721752662.X
Dec. 15, 2017 (CN) .......................... 201721755713.4

(56)  References Cited

FOREIGN PATENT DOCUMENTS

| | | | |
|---|---|---|---|
| CN | 107224675 | A | 10/2017 |
| CN | 206535011 | U | 10/2017 |
| EP | 2600356 | A1 | 6/2013 |
| EP | 2612692 | A1 | 7/2013 |
| EP | 3006961 | A1 | 4/2016 |
| EP | 3254729 | A1 | 12/2017 |
| EP | 3316665 | A1 | 5/2018 |
| JP | 2006047115 | A | 2/2006 |
| JP | 2007242422 | A * | 9/2007 |
| JP | 2009204428 | A | 9/2009 |
| JP | 2013019692 | A | 1/2013 |
| JP | 2014236913 | A | 12/2014 |
| JP | 2016107048 | A | 6/2016 |
| WO | 2017054557 | A1 | 4/2017 |

\* cited by examiner

NEUTRON CAPTURE THERAPY SYSTEM

CROSS-REFERENCE TO RELATED PATENT APPLICATION

This application is a continuation application of International Application No. PCT/CN2018/100963, filed on Aug. 17, 2018, which claims priority to Chinese Patent Application No. 201711350436.3, filed on Dec. 15, 2017; Chinese Patent Application No. 201721755713.4, filed on Dec. 15, 2017; Chinese Patent Application No. 201711348389.9, filed on Dec. 15, 2017; Chinese Patent Application No. 201721752662.X, filed on Dec. 15, 2017, the disclosures of which are hereby incorporated by reference.

FIELD

The present disclosure relates generally to a radioactive irradiation system, and, more particularly to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radio resistant malignant tumors (such as glioblastomamultiforme and melanoma).

For the purpose of reducing radiation damage to the normal tissue surrounding a tumor site, target therapy in chemotherapy has been employed in the radiotherapy. While for high-radio resistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

In an accelerator-based neutron capture therapy system, an accelerator accelerates a charged particle beam, the charged particle beam is accelerated enough to overcome the coulomb repulsion energy of a neutron generator atomic nucleus in a beam shaping assembly, and has nuclear reaction with the neutron generator to generate neutrons. Therefore, during the generation of neutrons, the neutron generator is irradiated by the accelerated charged particle beam with high power, the temperature of the neutron generator rises significantly, and the service life of the neutron generator is affected. Therefore, it is necessary to change the neutron generator, and the neutron generator irradiated by the accelerated charged particle beam at a high energy level inevitably holds a lot of radioactive rays. As a result, there are inevitable radioactive hazards during the changing of neutron generators.

Therefore, it is really necessary to provide a new technical solution so as to solve the foregoing problem.

The statements in this section merely provide background information related to the present disclosure and may not constitute prior art.

SUMMARY

To provide a neutron capture therapy system with reduced radioactive hazards, an embodiment of the present disclosure provides a neutron capture therapy system, including an accelerator configured to generate a charged particle beam, a neutron generator configured to react with the charged particle beam to generate a neutron beam, and a beam shaping assembly, wherein the beam shaping assembly includes an accommodating portion, a moderator adjacent to the neutron generator, a reflector surrounding the moderator, a thermal neutron absorber adjacent to the moderator, and a radiation shield and a beam exit disposed in the beam shaping assembly, a vacuum tube connected to the accelerator is provided at the accommodating portion, the neutron generator is disposed at an end of the vacuum tube, the vacuum tube transmits charged particles accelerated by the accelerator to the neutron generator to have a nuclear reaction with the neutron generator to generate neutrons, the neutrons form the neutron beam, the neutron beam defines a main axis, the moderator slows down the neutrons generated by the neutron generator to an epithermal neutron energy region, the reflector guides deflected neutrons back to the moderator to increase the intensity of an epithermal neutron beam, the radiation shield is configured to shield leaked neutrons and photons to reduce the dose to normal tissue in a non-irradiation area, the neutron generator moves between a first position and a second position, at the first position, the neutron generator is capable of reacting with the charged particle beam to generate neutrons, and at the second position, the neutron generator falls off the beam shaping assembly. With such an arrangement, only needs to move the neutron generator to fall off the beam shaping assembly, the neutron generator is able to be replaced. In some other implements, robotic arms, remote control or the like may be configured to prevent a worker from being exposed to radioactive rays.

Further, the length of the vacuum tube is able to be decreased along the irradiation direction of the neutron beam to provide a space for the neutron generator to move outside the accommodating portion along the irradiation direction of the neutron beam, and at the second position, the neutron generator is able to move outside the accommodating portion together with the vacuum tube to fall off the beam shaping assembly.

Further, the vacuum tube at least includes a first vacuum tube portion connected to the accelerator, a second vacuum tube portion accommodated in the accommodating portion of the beam shaping assembly and accommodates the neutron generator, and a third vacuum tube portion connects the first vacuum tube portion and the second vacuum tube portion, the third vacuum tube portion is detachable to provide the space for the neutron generator to move outside the accommodating portion, and at the second position, the neutron generator is able to move outside the accommodating portion together with the second vacuum tube portion and fall off the beam shaping assembly.

More particularly, to make it easy for the neutron generator to move outside the accommodating portion, a filler is filled between a periphery of the vacuum tube and an inner wall of the accommodating portion.

Further, the filler is made of a material capable of absorbing neutrons or reflecting neutrons.

Further, the neutron capture therapy system further includes a cooling device located in the accommodating portion and configured to cool the neutron generator, the filler is filled at the periphery of the vacuum tube and the inner wall of the accommodating portion to cover the cooling device, and at the second position, the cooling device and the filler fall off the accommodating portion together with the neutron generator.

Further, the cooling device includes a first cooling portion located at an end of the vacuum tube and in plane contact with the neutron generator, a second cooling portion and a third cooling portion located at two sides of the first cooling portion and respectively in communication with the first cooling portion, and the second cooling portion and the third cooling portion extend in a direction parallel to a neutron beam axis and are respectively located on an upper side and a lower side of the vacuum tube to form a "["-shaped structure with the first cooling portion.

To provide a movable space for the neutron generator to fall off the accommodating portion together with the vacuum tube, preferably, the neutron capture therapy system further includes a first shielding portion and a second shielding portion adjacent to the moderator and wrapped around a periphery of the accommodating portion, and the second shielding portion is capable of moving in a direction away from the vacuum tube with respect to the first shielding portion, the vacuum tube at least includes a first vacuum tube portion accommodated in the accommodating portion and accommodates the neutron generator and a second vacuum tube portion connects the first vacuum tube portion and the accelerator, the first vacuum tube portion is detachable from the second vacuum tube portion, and when the first vacuum tube portion is detached from the second vacuum tube portion and the second shielding portion moves to a position where the first vacuum tube portion is able to fall off the accommodating portion, the neutron generator falls off the beam shaping assembly together with the first vacuum tube portion. The second shielding portion moves to provide a movement space for the vacuum tube, and the second vacuum tube portion is detached from the first vacuum tube portion, the neutron generator falls off the beam shaping assembly together with the first vacuum tube portion of the vacuum tube.

Further, to further reduce the contact between a worker and the neutron generator and improve radioactive safety, the neutron capture therapy system further includes an accommodating device located vertically below the vacuum tube, the neutron generator moves outside the accommodating portion to fall in the accommodating device, and the accommodating device is made of a shielding material.

More particularly, the accommodating device includes a bottom portion and four side portions connected to the bottom portion, the bottom portion and the four side portions are connected to form an accommodating space having an opening, two rotating portions covering the opening are further disposed at the accommodating device, one end of the rotating portion is connected to any one of the side portions, the other end of the rotating portion is rotatable towards the accommodating space with respect to the connected side portion, in a natural state, the two rotating portions cover the accommodating space to form a top portion of the accommodating device, under an external force, the rotating portions rotate towards the accommodating space to be accommodated in the accommodating space, and when the external force disappears, the rotating portions restore the natural state.

Further, to reduce radioactive hazards, another embodiment of the present disclosure provides a neutron capture therapy system, including an accelerator configured to generate a charged particle beam, a neutron generator configured to react with the charged particle beam to generate a neutron beam, and a beam shaping assembly. The beam shaping assembly includes an accommodating portion, a moderator adjacent to the neutron generator, a reflector surrounding the moderator, a thermal neutron absorber adjacent to the moderator, a radiation shield disposed in the beam shaping assembly, and a shielding device and a beam exit adjacent to the beam shaping assembly, a vacuum tube connected to the accelerator is provided at the accommodating portion, the neutron generator is disposed at an end of the vacuum tube, the vacuum tube transmits charged particles accelerated by the accelerator to the neutron generator to have a nuclear reaction with the neutron generator to generate neutrons, the neutrons form the neutron beam, the neutron beam defines a main axis, the moderator slows down the neutrons generated by the neutron generator to an epithermal neutron energy region, the reflector guides deflected neutrons back to the moderator to increase the intensity of an epithermal neutron beam, the radiation shield is configured to shield leaked neutrons and photons to reduce the dose to normal tissue in a non-irradiation area, the neutron generator moves between a first position and a second position, at the first position, the neutron generator reacts with the charged particle beam to generate neutrons, at the second position, the neutron generator falls off the beam shaping assembly, and the beam shaping assembly and the shielding device keep shielding the neutron generator as the neutron generator moves from the first position to the second position to prevent a worker from the leakage irradiation of the neutron generator.

When the neutron generator is in the beam shaping assembly, the radiation shield in the beam shaping assembly is capable of shielding radioactive rays leaked from the neutron generator to protect a worker from irradiation by radioactive rays. After the neutron generator falls off the beam shaping assembly, the radiation shield is not able to shield the neutron generator, in this case, the shielding device is configured to shield the neutron generator, thereby keeping the neutron generator in a shielded state as the neutron generator moves from the first position to the second position, so as to prevent a worker from leakage irradiation from the neutron generator.

Particularly, the vacuum tube at least includes a first vacuum tube portion connected to the accelerator, a second vacuum tube portion accommodated in the accommodating portion of the beam shaping assembly and accommodates the neutron generator, and a third vacuum tube portion connects the first vacuum tube portion and the second vacuum tube portion, the third vacuum tube portion is detachable to provide a space for the neutron generator to move outside the accommodating portion, and at the second position, the neutron generator is capable of moving outside the accommodating portion together with the second vacuum tube portion to fall off the beam shaping assembly.

Further, the shielding device includes a bottom wall and a first side wall and a second side wall connected to the bottom wall and disposed opposite to each other, the bottom wall and the two side walls form a U-shaped structure having a first opening, a second opening, and a third opening, the first opening is adjacent to the first vacuum tube portion, the second opening is adjacent to the second vacuum tube portion, and the third vacuum tube portion passes through the third opening. In the present disclosure, preferably, the third vacuum tube portion is detached after the shielding device is disposed outside the vacuum tube. During actual operations, the shielding device may be alternatively installed after the third vacuum tube portion is detached.

Particularly, the shielding device further includes a top wall disposed opposite to the bottom wall and a third side wall and a fourth side wall connect the bottom wall and the top wall, the third side wall and the fourth side wall are disposed opposite to each other, the bottom wall, the top wall, and the four side walls form a shielding space, the top wall is rotatable around the second side wall or the fourth side wall in a direction away from the shielding space, and the first side wall and the third side wall are respectively rotatable around the bottom wall in the direction away from the shielding space, and the shielding device forms the U-shaped structure. When the shielding device is located between the first vacuum tube portion and a second vacuum tube portion, the shielding device forms the U-shaped structure; and when both of the neutron generator and the second vacuum tube portion are located at the shielding device, the shielding device forms the shielding space to shield the neutron generator.

To make it easy for the neutron generator to move outside the accommodating portion, a filler is filled between a periphery of the vacuum tube and an inner wall of the accommodating portion, the neutron capture therapy system further includes a cooling device located in the accommodating portion and configured to cool the neutron generator, the filler is filled at the periphery of the vacuum tube and the inner wall of the accommodating portion to cover the cooling device, and when the neutron generator moves into the shielding device, the cooling device and the filler move into the shielding device together with the neutron generator.

Further, the filler is made of a material capable of absorbing neutrons or reflecting neutrons.

Further, the neutron capture therapy system further includes a cooling device located in the accommodating portion and configured to cool the neutron generator, and the filler is filled at the periphery of the vacuum tube and the inner wall of the accommodating portion to cover the cooling device.

Particularly, the cooling device includes a first cooling portion located at an end of the vacuum tube and in plane contact with the neutron generator, a second cooling portion and a third cooling portion located on two sides of the first cooling portion and respectively in communication with the first cooling portion, and the second cooling portion and the third cooling portion extend in a direction parallel to a neutron beam axis and are respectively located on an upper side and a lower side of the vacuum tube to form a "["-shaped structure with the first cooling portion.

Further, to further reduce contact between a worker and the neutron generator and improve radioactive safety, the neutron capture therapy system further includes an accommodating device located below the vacuum tube, the neutron generator moves from the accommodating portion to the shielding device to fall in the accommodating device, and the accommodating device is made of a shielding material.

Further, the accommodating device includes a bottom portion and four side portions connected to the bottom portion, the bottom portion and the four side portions are connected to form an accommodating space having an opening, two rotating portions covering the opening are further disposed at the accommodating device, one end of the rotating portion is connected to a side portion, the other end of the rotating portion is rotatable towards the accommodating space with respect to the connected side portion, in a natural state, the two rotating portions cover the accommodating space to form a top portion of the accommodating device, under an external force, the rotating portions rotate towards the accommodating space to be accommodated in the accommodating space, and when the external force disappears, the rotating portions restore the natural state.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Figure 1:
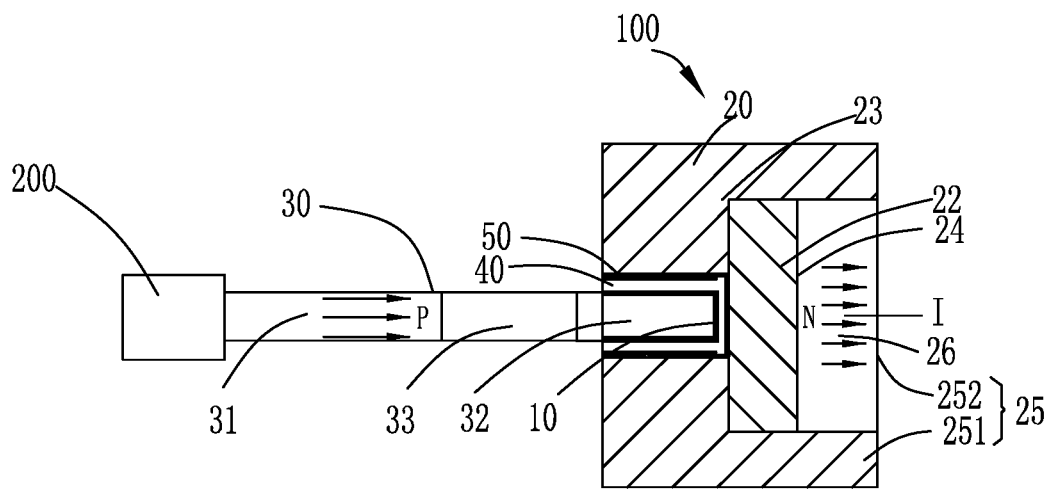
FIG. 1 is a schematic view of a first embodiment of a neutron capture therapy system according to the present disclosure, where a neutron generator is a first position.

The embodiments of the present disclosure are further described in detail below with reference to the accompanying drawings, so that those skilled in the art can implement the technical solutions according to the description.

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7Li~(p, n)^7Be$ and $^9Be~(p, n)^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7Li~(p, n)^7Be$ asks for more than $^9Be~(p, n)^9B$ does because of low melting point and poor thermal conductivity coefficient of the metal (lithium) target. In these embodiments of the present disclosure is $^7Li~(p, n)^7Be$.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux $>1\times10^9$ n/cm$^2$s
Fast neutron contamination $<2\times10^{-13}$ Gy-cm$^2$/n
Photon contamination $<2\times10^{-13}$ Gy-cm$^2$/n
Thermal to epithermal neutron flux ratio $<0.05$
Epithermal neutron current to flux ratio $>0.7$ Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$Gy-cm$^2$/n 3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

To solve the problem of replacing the neutron generator and at the same time reducing the exposure of workers to radioactive rays, the present disclosure provides a neutron capture therapy system.

Main radiation that a target replacement person is exposed is radioactive rays generated from nuclear reactions that occur after a charged particle beam is irradiated to a neutron generator. Therefore, the present disclosure is intended to describe the detachment of the neutron generator after nuclear reactions take place rather than to describe the installation of a new neutron generator.

As shown in FIG. 1, a neutron capture therapy system 100 includes an accelerator 200 configured to generate a charged particle beam P, a neutron generator 10 reacts with the charged particle beam P to generate a neutron beam N, and a beam shaping assembly 20. The beam shaping assembly 20 includes an accommodating portion 21, a moderator 22 adjacent to the neutron generator 10, a reflector 23 surrounding the moderator 22, a thermal neutron absorber 24 adjacent to the moderator 22, and a radiation shield 25 and a beam exit 26 disposed in the beam shaping assembly 20. The accommodating portion 21 accommodates a vacuum tube 30 connected to the accelerator 200, and the neutron generator 10 is disposed at an end of the vacuum tube 30 to be adjacent to the moderator 22. The vacuum tube 30 transmits charged particles P accelerated by the accelerator 200 to the neutron generator 10, the accelerator 200 accelerates the charged particles P to an energy that is sufficient to overcome the force of the atomic nuclei of the neutron generator, the charged particles has a 7Li(p,n)7Be nuclear reaction with the neutron generator 12 to generate neutrons, the neutrons form the neutron beam N, the neutron beam N defines a main axis I. The moderator 22 slows down the neutrons generated by the neutron generator 10 to an epithermal neutron energy region. The reflector 23 guides deflected neutrons back to the moderator 22 to increase the intensity of the epithermal neutron beam. The thermal neutron absorber 24 is configured to absorb thermal neutrons to avoid excessive dose to superficial normal tissue during treatment. The radiation shield 25 is configured to shield leaked neutrons and photons to reduce the dose to normal tissue in a non-irradiation area.

Figure 2:
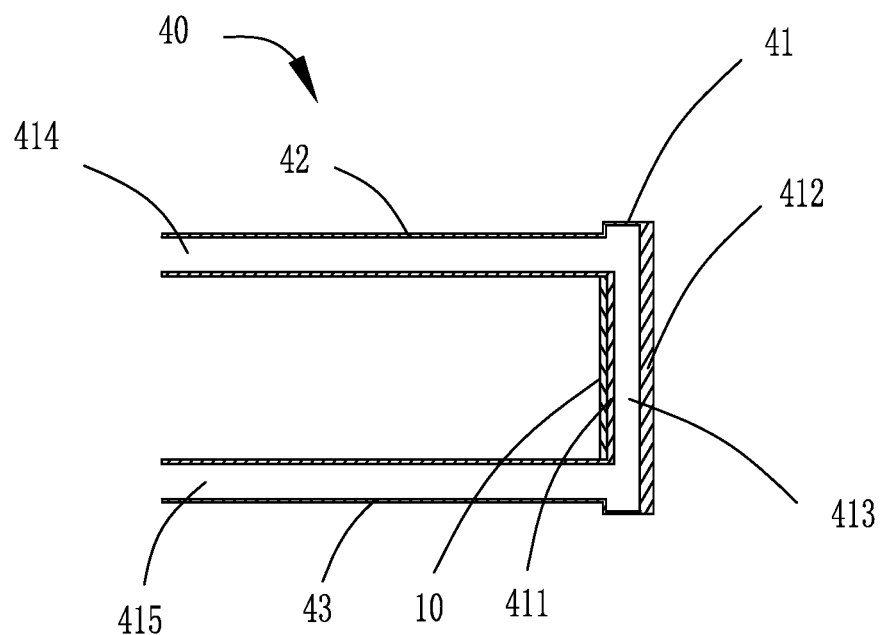
FIG. 2 is a sectional view showing that a cooling device in FIG. 1 is in a direction perpendicular to an irradiation direction of a neutron beam.

Referring to FIG. 2, the neutron capture therapy system 100 further includes a cooling device 40 configured to cool the neutron generator 10 to increase the service life of the neutron generator.

The cooling device 40 includes a first cooling portion 41 located at an end of the vacuum tube 30 and in plane contact with the neutron generator 10 and a second cooling portion 42 and a third cooling portion 43 located on two sides of the first cooling portion 41 and respectively in communication with the first cooling portion 41. A gap exists between a periphery of the vacuum tube 30 and an inner wall of the accommodating portion 21, the second cooling portion 42 and the third cooling portion 43 extend in a direction parallel to the neutron beam axis I in the gap and are respectively located on an upper side and a lower side of the vacuum tube 30 to form a "["-shaped structure with the first cooling portion 41. To enable the cooling device 40 to cool the neutron generator 10 at an end of the vacuum tube 30 and at the same time to ensure the neutron beam quality of the beam shaping assembly 20, part of the vacuum tube 30 is inserted in the moderator 22 (not shown). The second cooling portion 42 inputs a cooling medium into the first cooling portion 41, and the third cooling portion 43 outputs the cooling medium in the first cooling portion 41. The first cooling portion 41 is located between the neutron generator 10 and the moderator 22, one side of the first cooling portion 41 is directly in plane contact with the neutron generator 10, and the other side of the first cooling portion 41 is in contact with the moderator 22.

The first cooling portion 41 includes a first contacting portion 411, a second contacting portion 412, and a cooling groove 413 located between the first contacting portion 411 and the second contacting portion 412, the cooling groove 413 is configured to allow the cooling medium to pass through. The first contacting portion 411 is in direct contact with the neutron generator 10, and the second contacting portion 412 and the moderator 22 may be in direct contact or may be in indirect contact through air. The cooling groove 413 has an inputting groove 414 in communication with the second cooling portion 42 and an outputting groove 415 in communication with the third cooling portion 43. The first contacting portion 411 is made of a thermal conductive material. The first contacting portion 411 is made of a thermal conductive material (such as Cu, Fe, and Al with high thermal conductivity) or a material capable of heat conducting and blistering inhibiting, the second contacting portion 412 is made of a material capable of blistering inhibiting, and the material is any of Fe, Ta or V. The temperature of the neutron generator 10 raises up after being irradiated by accelerated charged particles at a high energy level and generates heat, the heat is brought away by the first contacting portion 411, and the cooling medium flows in the cooling groove 413 and takes away the heat to cool the neutron generator 10. In this embodiment, the cooling medium is water.

Figure 5:
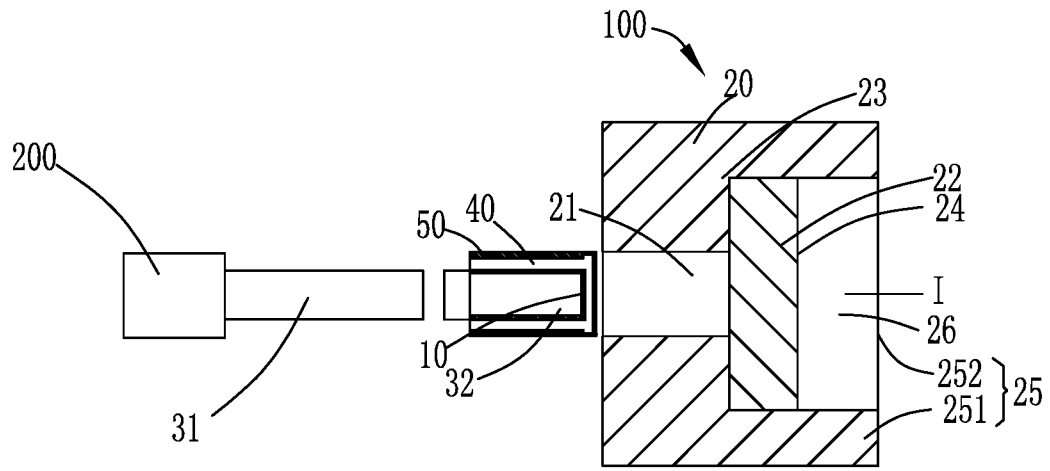
FIG. 5 is a schematic diagram showing that a second vacuum tube portion and the neutron generator move outside an accommodating portion after the third vacuum tube portion in FIG. 4 is detached, that is, the neutron generator is at a second position.

Referring to FIG. 1 and FIG. 5, FIG. 1 is a schematic view shows the neutron generator located at a first position, and FIG. 5 is a schematic view shows the neutron generator located at a second position. The neutron generator 10 moves between the first position and the second position, at the first position, the neutron generator 10 reacts with the charged particle beam to generate neutrons, and at the second position, the neutron generator 10 separates from the beam shaping assembly 20.

Figure 3:
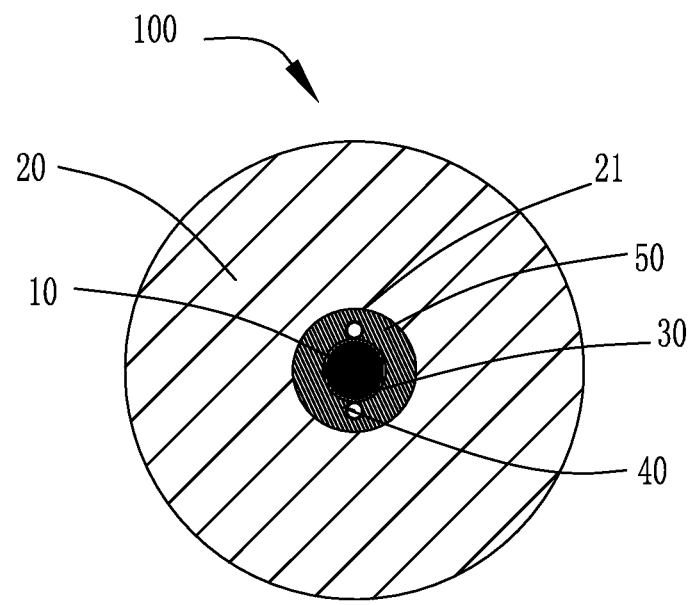
FIG. 3 is a partial sectional view of the neutron capture therapy system in a direction perpendicular to an irradiation direction of a neutron beam in FIG. 1.

Referring to FIG. 3, a gap is formed between the accommodating portion 21 and an outer wall of the vacuum tube 30. A filler 50 is filled in the gap. The filler 50 is wrapped around the outer wall of the vacuum tube 30 and the cooling device 40. The material of the filler 50 is capable of absorbing or reflecting neutrons, such as lead alloy or aluminum alloy. In this embodiment, the content of lead in the lead alloy is more than or equal to 85%, and the content of aluminum in the aluminum alloy is more than or equal to 85%. In one aspect, the filler 50 reflects neutrons that are reflected or scattered in the gap to the moderator 22 or the reflector 23, the yield of epithermal neutrons is increased and the irradiation time that an irradiated body needs is reduced. In another aspect, neutrons leakage outside the beam shaping assembly 20 to adversely affect the instruments of the neutron capture therapy system is avoided, thereby the radioactive safety is improved. In addition, when the neutron generator 10 moves outside the accommodating portion 21, the cooling device 40 and the filler 50 move outside the accommodating portion 21 together with the neutron generator 10 to fall off the beam shaping assembly 20.

Figure 4:
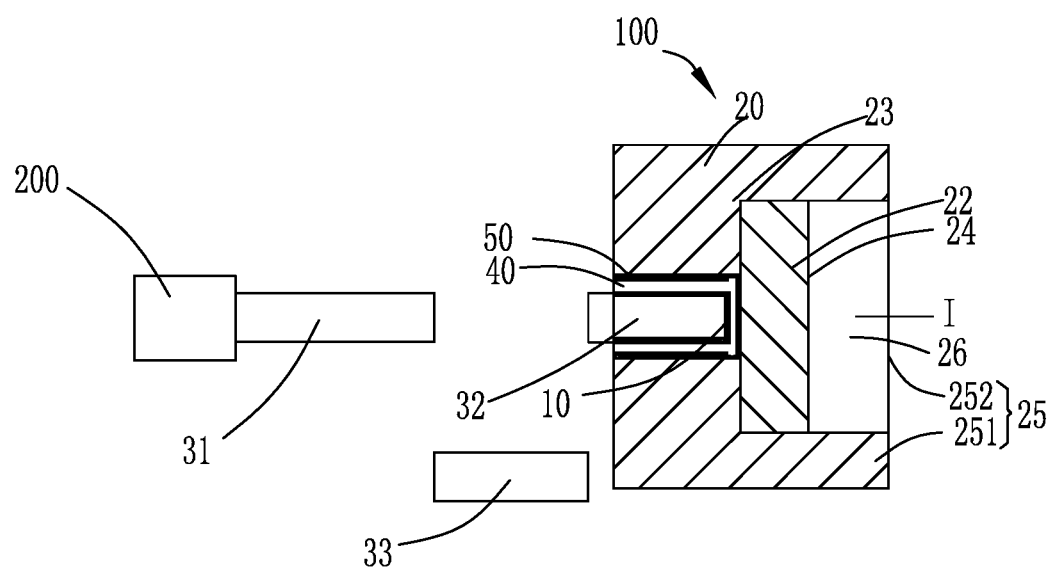
FIG. 4 is a schematic diagram showing that a third vacuum tube portion of a vacuum tube in FIG. 1 is detached.

In a first embodiment, referring to FIG. 1, FIG. 4, and FIG. 5, the vacuum tube 30 includes a first vacuum tube portion 31 connected to the accelerator 200, a second vacuum tube portion 32 accommodated in the accommodating portion 21, and a third vacuum tube portion 33 connects the first vacuum tube portion 31 and the second vacuum tube portion 32. One end of the second vacuum tube portion 32 is adjacent to the moderator 22, the other end of the second vacuum tube portion 32 extends from the accommodating portion 21 and connects to the third vacuum tube portion 33, the neutron generator 10 is at an end of the second vacuum tube portion 32 and is adjacent to the moderator 22. The third vacuum tube portion 33 is detachable from the first vacuum tube portion 31 and the second vacuum tube portion 32 to decrease the overall length of the vacuum tube 30, so as to provide a space for the neutron generator 10 to move outside the accommodating portion 21 in a direction opposite to the irradiation direction of the neutron beam N. After the third vacuum tube portion 33 is detached from the first vacuum tube portion 31 and the second vacuum tube portion 32, the second vacuum tube portion 32 moves outside the accommodating portion 21 in the direction opposite to the irradiation direction of the neutron beam N to fall off the beam shaping assembly 20.

In this embodiment, the vacuum tube 30 falls off the beam shaping assembly 20 because a space is shaped for the first vacuum tube portion 31 to move outside the accommodating portion 21 in the direction opposite to the irradiation direction of the neutron beam N after the second vacuum tube portion 32 is detached. That is, the overall length of the vacuum tube 30 is changed to make a space for the neutron generator 10. In another embodiment of changing the overall length of the vacuum tube, the vacuum tube may be disposed to be retractable in the irradiation direction of the neutron beam (For example, part of the vacuum tube located outside the beam shaping assembly is disposed as a telescopic corrugated pipe. The overall length of the vacuum tube decreases when the corrugated pipe is compressed, and the neutron generator moves outside the beam shaping assembly together with the vacuum tube in the direction opposite the irradiation direction of the neutron beam). Details are not described herein again.

Figure 6:
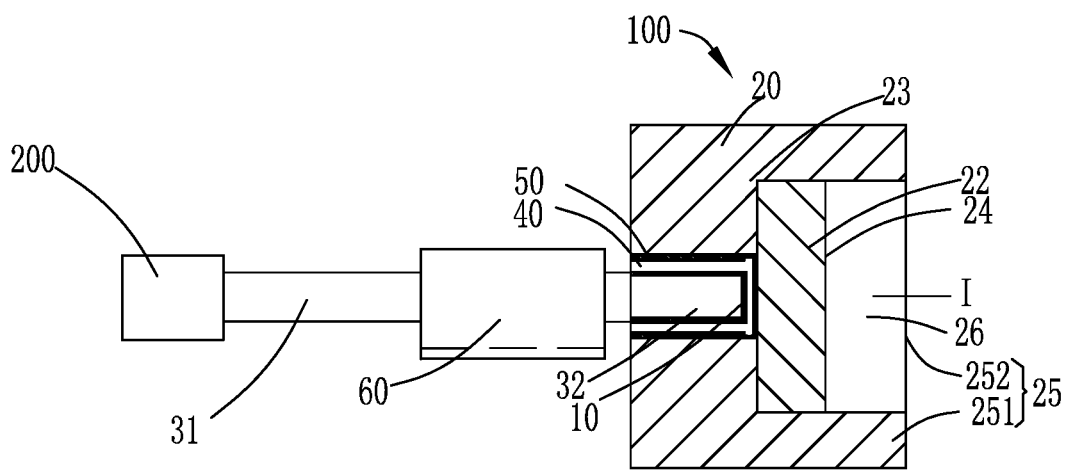
FIG. 6 is a schematic view of a second embodiment of a neutron capture therapy system according to the present disclosure, where a shielding device is installed between a first vacuum tube portion and a second vacuum tube portion.
Figure 7:
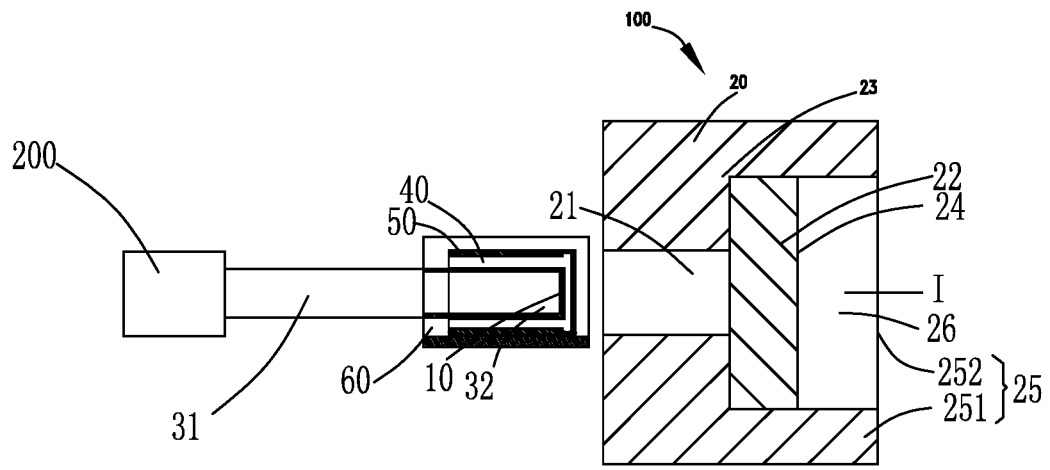
FIG. 7 is a schematic diagram showing that the second vacuum tube portion and a neutron generator in FIG. 6 move into a shielding device.
Figure 8:
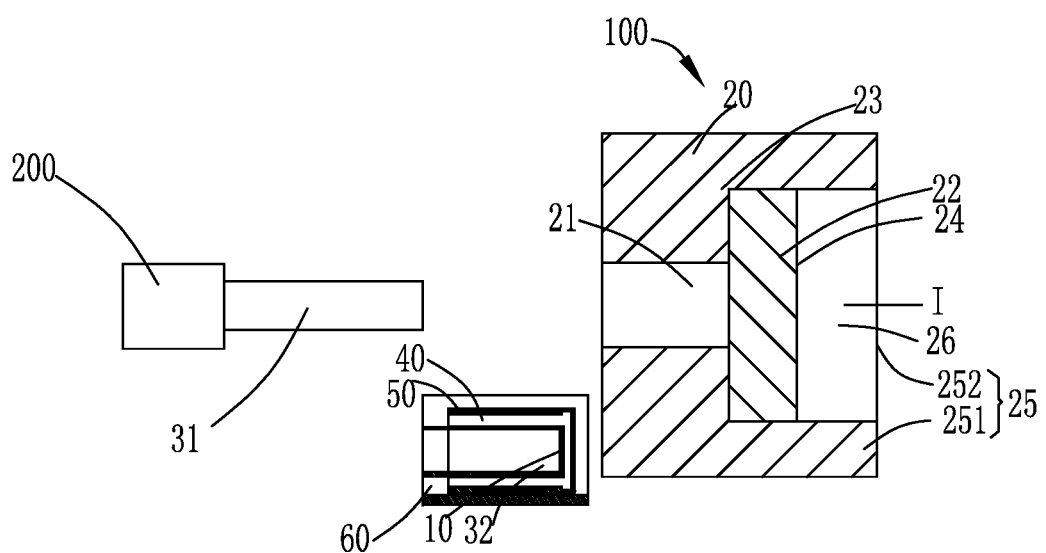
FIG. 8 is a schematic diagram showing that the shielding device that accommodates the second vacuum tube portion and a neutron generator in FIG. 6 is detached.

FIG. 6 to FIG. 8 are schematic views of a second embodiment of the neutron capture therapy system of the present disclosure. To further reduce safety hazards of radioactive rays for workers, the neutron capture therapy system 100 further includes a shielding device 60.

Figure 9:
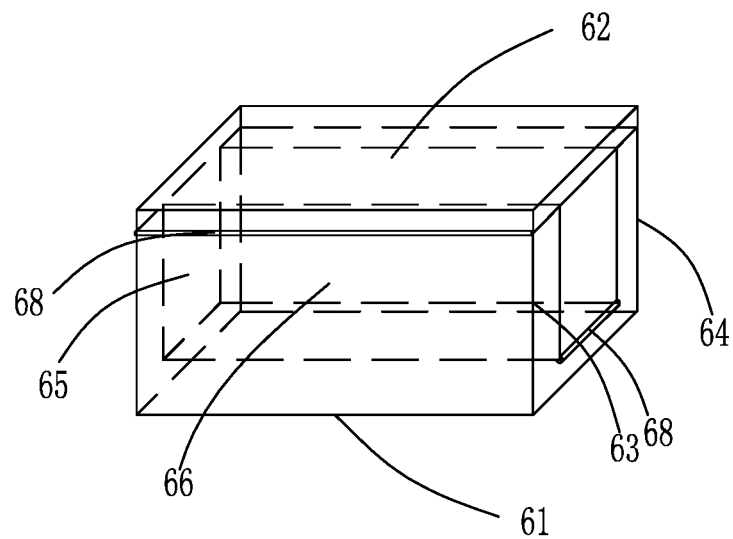
FIG. 9 is a schematic perspective view of the shielding device in FIG. 6.

Referring to FIG. 9, the shielding device 60 includes a bottom wall 61, a top wall 62 opposite to the bottom wall 61, and a first side wall 63, a second side wall 64, a third side wall 65 and a fourth side wall 66 connect the bottom wall 61 and the top wall 62. The first side wall 63 and the third side wall 65 are opposite to each other, the second side wall 64 and the fourth side wall 66 are opposite to each other, and the bottom wall 61, the top wall 62, and the four side walls are connected to form a shielding space 67. The top wall 62 is rotatable around the second side wall 64 or the fourth side wall 66 in a direction away from or towards the shielding space 67, and the first side wall 63 and the third side wall 65 are respectively rotatable around the bottom wall 61 in a direction away from or towards the shielding space 67. The top wall 62, the first side wall 63, and the third side wall 65 rotate by means of rotating members 68 installed in the bottom wall 61, the first side wall 63, and the third side wall 65. When the top wall 62, the first side wall 63, and the third side wall 65 rotate around the rotating member 68 in the direction away from the shielding space 67, the shielding device 60 form a U-shaped structure to make it convenient for a worker to move the first vacuum tube portion 31 outside the beam shaping assembly 20 and keep the neutron generator 10 moving in the shielding space 67.

Figure 10:
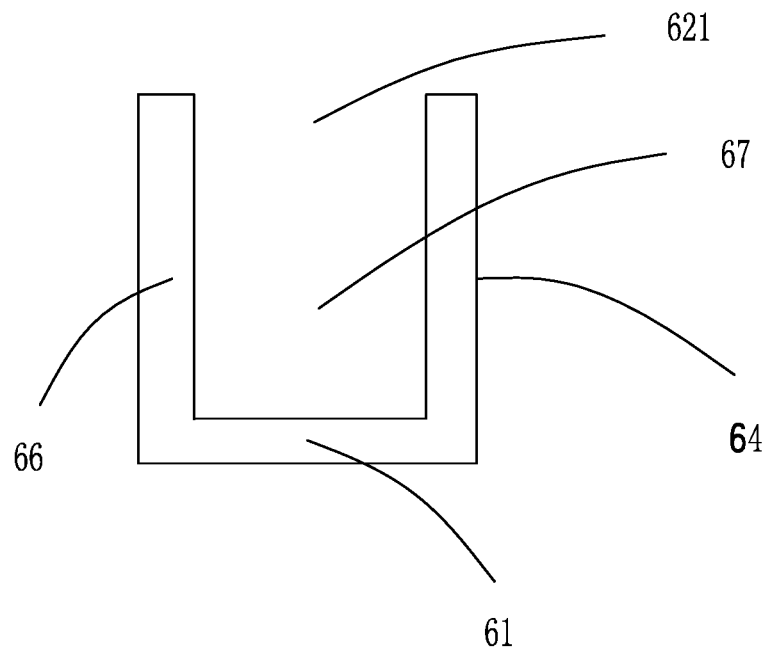
FIG. 10 is a schematic diagram of another embodiment of the shielding device shown in FIG. 9.
Figure 11:
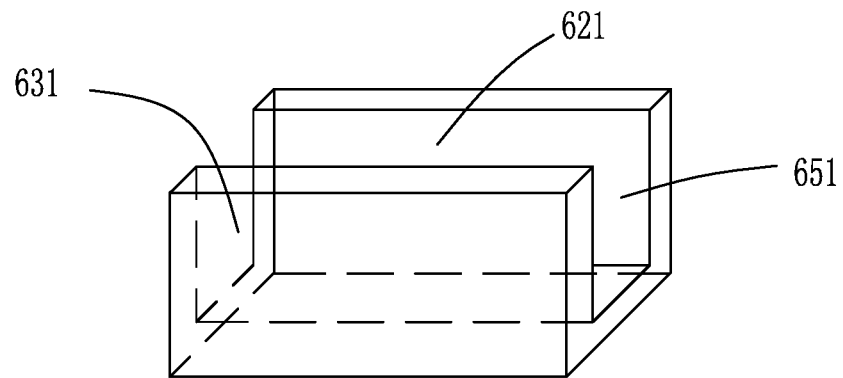
FIG. 11 is a schematic view of the shielding device shown in FIG. 10.
Figure 12:
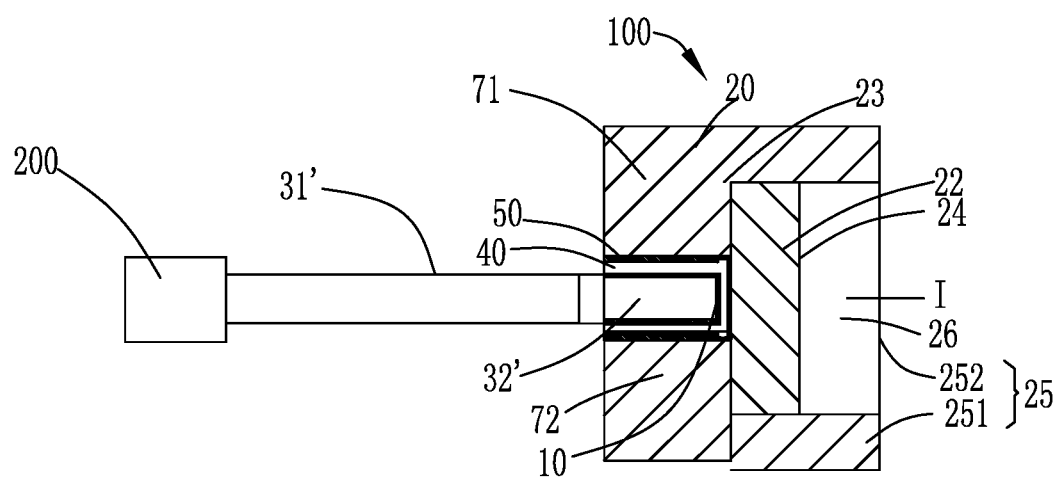
FIG. 12 is a schematic view of a third embodiment of a neutron capture therapy system according to the present disclosure.
Figure 13:
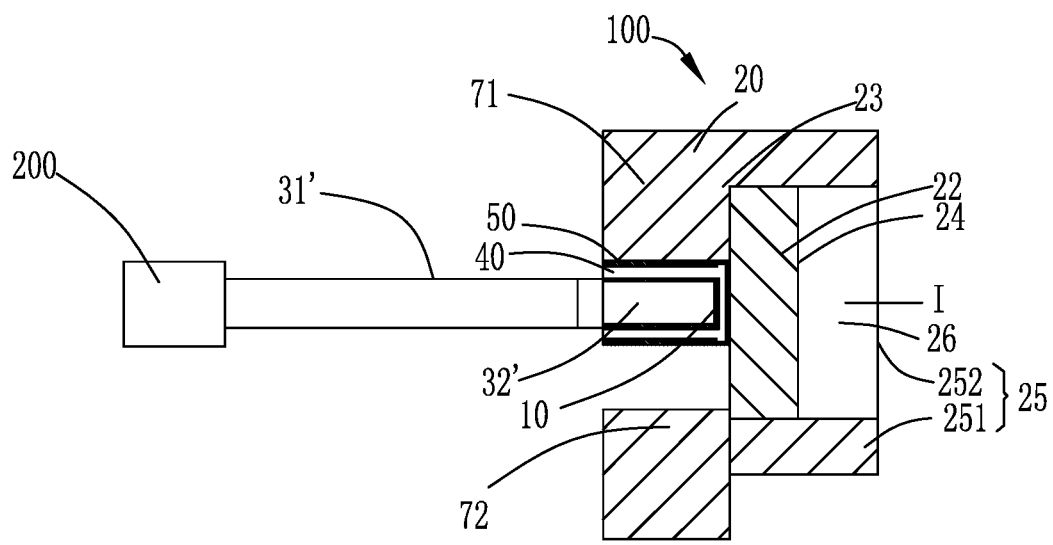
FIG. 13 is a schematic view showing that a second shielding portion in FIG. 12 moves in a direction away from a neutron generator with respect to a first shielding portion.
Figure 14:
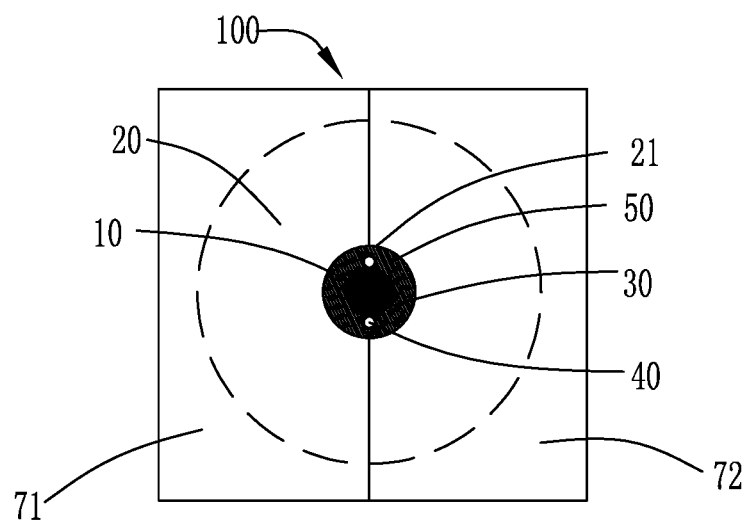
FIG. 14 is a partial sectional view of the neutron capture therapy system in a direction perpendicular to an irradiation direction of a neutron beam in FIG. 12.
Figure 15:
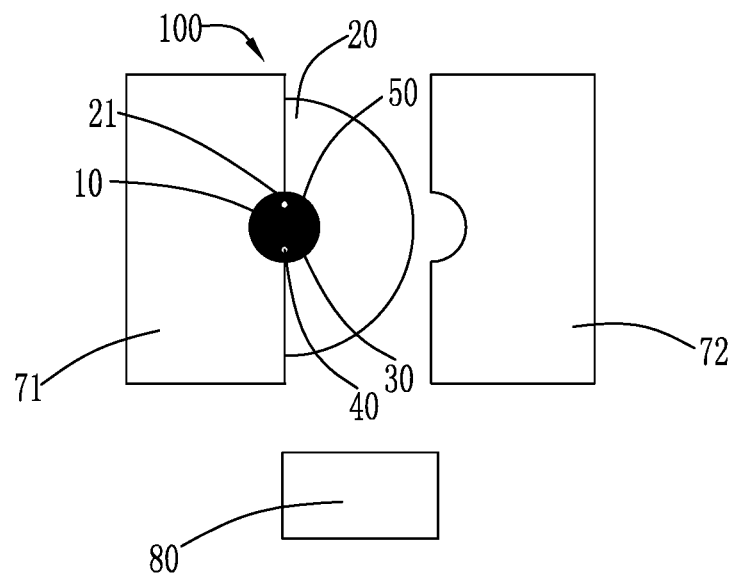
FIG. 15 is a partial sectional view of the neutron capture therapy system in a direction perpendicular to an irradiation direction of a neutron beam in FIG. 13.
Figure 16:
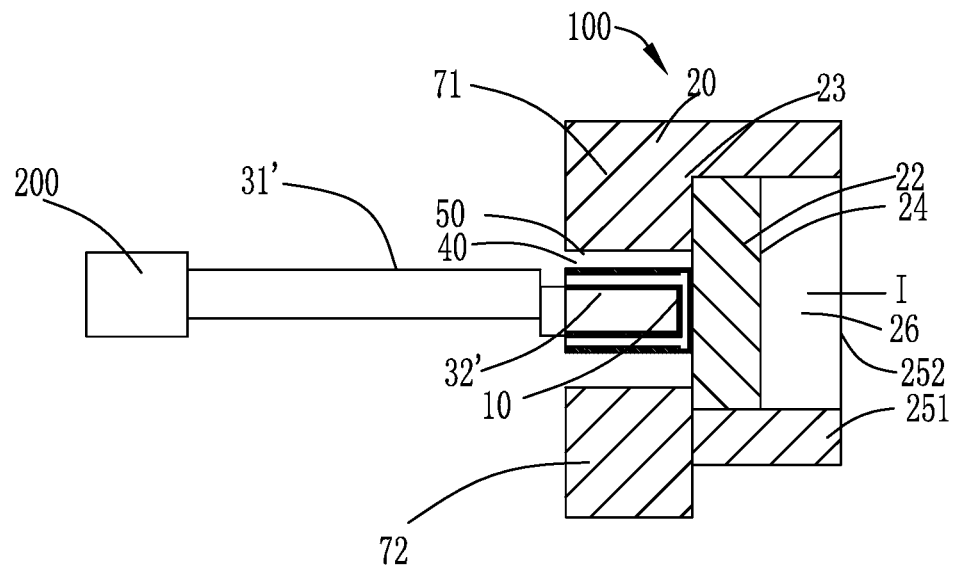
FIG. 16 is a schematic diagram showing that a first vacuum tube portion and a neutron generator move outside an accommodating space after the second shielding portion shown in FIG. 14 moves.
Figure 17:
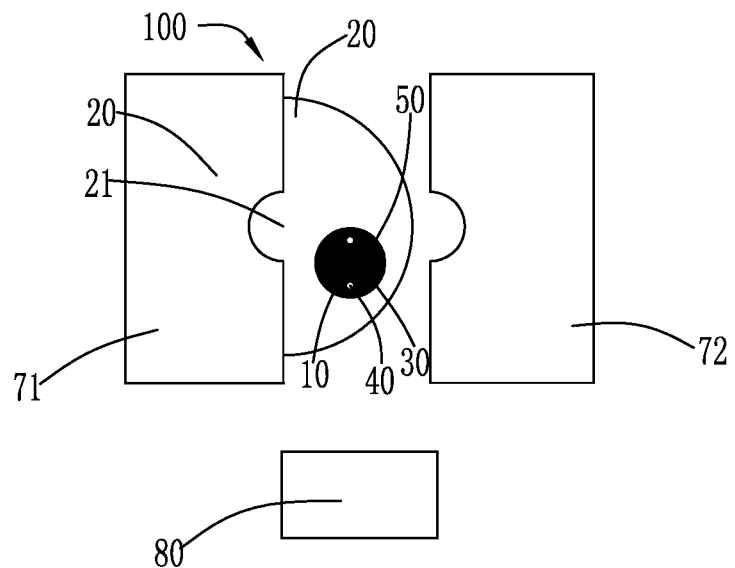
FIG. 17 is a partial sectional view of the neutron capture therapy system in a direction perpendicular to the irradiation direction of the neutron beam in FIG. 16.

Certainly, in another embodiment (referring to FIG. 10 and FIG. 11) of the shielding device 60, the shielding device 60 includes only the bottom wall 61 and the two side walls (64, 66) connected to the bottom wall 61 and disposed opposite to each other. The bottom wall 61 and the two side walls form a first opening 631, a second opening 651 opposite to the first opening 631, and a third opening 621 opposite to the bottom wall 61. That is, the bottom wall 61 and the two side walls form the U-shaped structure, and the U-shaped structure has the shielding space 67. The first opening 631 is adjacent to the first vacuum tube portion 31, the second opening 651 is adjacent to the second vacuum tube portion 32, the third vacuum tube portion 33 passes through the third opening, and the third opening 621 is configured for a worker to move the second vacuum tube portion 32 to the shielding space 67. In this embodiment, the shielding device 60 is located at the periphery of the vacuum tube 30. When the neutron generator needs to be changed, the worker removes the third vacuum tube portion and moves the second vacuum tube portion 32 until the neutron generator 10, the filler 50, and the cooling device 40 move together with the second vacuum tube portion 32 and are accommodated in the shielding space 67 of the shielding device 60, then the worker removes the shielding device 60 from the first vacuum tube portion 31, and the top wall 62, the first side wall 63, and the third side wall 65 respectively rotate to enable the top wall 60, the first side wall 63, and the third side wall 65 to respectively cover the shielding space 67 to completely shield against radioactive rays in the shielding space 67. The shielding device 60 shields radioactive rays that remain in the neutron generator 10 after nuclear reaction, thereby reducing safety hazards of radioactive rays for workers. Certainly, during actual operations, the shielding device 60 may also be alternatively disposed between the first vacuum tube portion 31 and the second vacuum tube portion 32 after the third vacuum tube portion 33 is detached.

The setting of the shielding device 60 may be achieved by the connection (abutting) between the first opening 631 and the first vacuum tube portion 31 and the connection (abutting) between the second opening 651 and the second vacuum tube portion 32 (the beam shaping assembly 20), or an additional structure capable of holding the shielding device 60 at the periphery of the vacuum tube 30.

Because when the worker changes the neutron generator, he stands on one side of the beam shaping assembly, when the worker moves the second vacuum tube portion, both the bottom wall and the side walls of a shielding device are capable of shielding radioactive rays remain in the neutron generator. After the neutron generator falls into the shielding space together with the second vacuum tube portion, the top wall, the first side wall, and the third side wall rotate to completely surround the shielding space with the shielding material, thereby radioactive hazards for workers is further reduced. Certainly, the shielding device 60 with the U-shaped structure is also sufficient to shield the radioactive rays that may irradiate the worker and reduce radioactive hazards for the worker.

FIG. 12 to FIG. 17 are schematic views of a third embodiment of a neutron capture therapy system according to the present disclosure. A neutron capture therapy system 100' further includes a shielding portion adjacent to the moderator 22, and the shielding portion is wrapped around the periphery of the accommodating portion 21. The shielding portion includes a first shielding portion 71 and a second shielding portion 72, and the second shielding portion 72 is capable of moving with respect to the first shielding portion 71 in a direction away from the vacuum tube 30 to enable the neutron generator 10 to fall off the accommodating portion 21. The vacuum tube 30 at least includes a first vacuum tube portion 31' connected to the accelerator 200 and a second vacuum tube portion 32' connected to the first vacuum tube portion 31' and accommodated in the accommodating portion 21. After the first vacuum tube portion 31' is detached from the second vacuum tube portion 32', and when the second shielding portion 72 moves to the first vacuum tube portion 31' in a direction away from the neutron generator 10 and is able to fall off the accommodating portion 21, the neutron generator 10 moves outside the accommodating portion 21 together with the second vacuum tube portion 32' and fall off the beam shaping assembly 20. The filler and the cooling device also fall off the beam shaping assembly 20 together with the neutron generator 10.

To reduce safety hazards of radioactive rays for workers, in embodiment 2, the neutron capture therapy system further includes the shielding device 60 and an accommodating device 80 located below the vacuum tube 30, the neutron generator 10 falls off the accommodating portion 21 and accommodates in the accommodating device 80, the accommodating device 80 is made of a shielding material.

Figure 18:
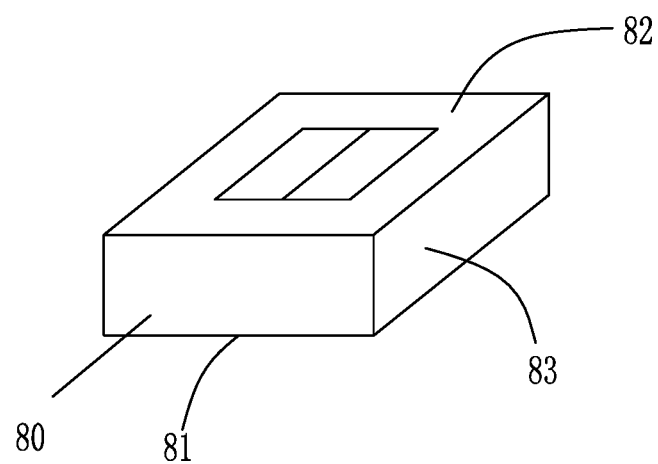
FIG. 18 is a schematic diagram of an accommodating device in FIG. 15 in a natural state.
Figure 19:
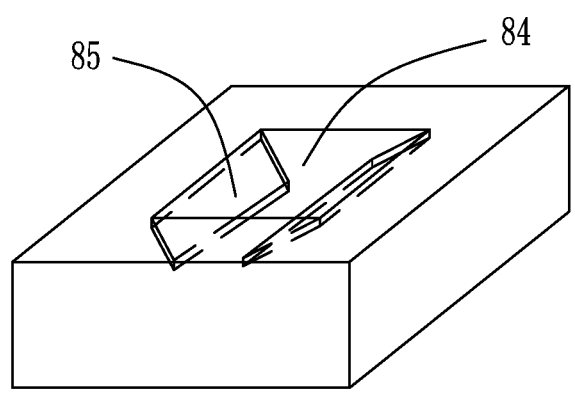
FIG. 19 is a schematic diagram showing that an external force has been put to the accommodating device in FIG. 18.

Referring to FIG. 18 to FIG. 19, the accommodating device 80 includes a bottom portion 81, a top portion 82 opposite to the bottom portion 81, and four side portions 83 connected to the bottom portion 81 and the top portion 82. The bottom portion 81, the top portion 82, and the four side portions 83 are connected to form an accommodating space 84 of the accommodating device 80. An opening is further provided in the top portion 82 of the accommodating device 80. Two rotating portions 85 disposed opposite to each other cover the opening. One end of each rotating portion 85 is connected to the top portion 82, and the other end of the rotating portion 85 is rotatable with respect to the top portion towards the accommodating space 84. In a natural state, the two rotating portions 85 are above the accommodating space 84 to cover the opening. Under an external force, the rotating portions 85 rotate towards the accommodating space 84 to be accommodated in the accommodating space 84, and when the external force disappears, the rotating portions 85 restore the natural state. For the movement of the rotating portions 85, an axis member (not shown) may be disposed at the top portion 82 to enable the rotating member 85 to rotate into the accommodating space 84 or cover the upper opening of the accommodating space 84. Details are not described herein gain.

Certainly, the accommodating device in the third embodiment may also be accommodated in the first embodiment and the second embodiment to further reduce a probability of direct contact between a worker and radioactive rays.

In the neutron capture therapy system, the accelerator is configured to accelerate the charged particle beam P. In a preferred embodiment, the neutron generator 31 is made of lithium. The charged particle beam is accelerated enough to overcome coulomb repulsive force of the neutron generator atomic nuclei, and has a $^7Li(p,n)^7Be$ nuclear reaction with the neutron generator 31 to generate neutrons. The beam shaping assembly 20 moderates the neutrons to an epithermal neutron energy region, and reduces the thermal neutrons and fast neutrons. As shown in FIG. 3, the neutron generator 10 includes a lithium target layer 101 and an anti-oxidation layer 102 located on one side of the lithium target layer 101 and is configured to protect the lithium target layer 101 from oxidation. The anti-oxidation layer 102 of the neutron generator 10 is made of Al or stainless steel.

The moderator 22 is made of a material with a large fast neutron reaction cross section and a small epithermal neutron reaction cross section, the reflector 23 is made of a material with high neutron reflectivity, and the thermal neutron absorber 24 is made of a material with a large thermal neutron reaction cross section. In a preferred embodiment, the moderator 22 is made of at least one of $D_2O$, $AlF_3$, Fluental™, $CaF_2$, $Li_2CO_3$, $MgF_2$, and $Al_2O_3$, the reflector 23 is made of at least one of Pb or Ni, and the thermal neutron absorber 24 is made of $^6Li$.

The radiation shield 25 includes a photon shield 251 and a neutron shield 252. Preferably, the radiation shield 25 includes a photon shield 251 made of lead (Pb) and a neutron shield 252 made of polyethylene (PE).

To facilitate the description of the present disclosure, the same reference numeral represents the same component in the present disclosure.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system, comprising:
    an accelerator configured to generate a charged particle beam;
    a neutron generator configured to react with the charged particle beam to generate neutrons, wherein the neutrons form a neutron beam, and the neutron beam defines a main axis;
    a vacuum tube connected to the accelerator; and
    a beam shaping assembly which comprises:
        an accommodating portion;
        a moderator adjacent to the neutron generator to moderate the neutrons generated by the neutron generator to an epithermal neutron energy region;
        a reflector surrounding the moderator to guide deflected neutrons back to the moderator to increase an intensity of epithermal neutrons;
        a thermal neutron absorber adjacent to the moderator;
        a radiation shield configured to shield leaked neutrons and photons to reduce dosage to normal tissue in a non-irradiation area; and
        a beam exit disposed in the beam shaping assembly,
    wherein the vacuum tube is provided at the accommodating portion, the neutron generator is disposed at an end of the vacuum tube, the vacuum tube transmits charged particles accelerated by the accelerator to the neutron generator, wherein the neutron generator moves between a first position where the neutron generator reacts with the charged particle beam to generate neutrons and a second position where the neutron generator separates from the beam shaping assembly.

2. The neutron capture therapy system according to claim 1, wherein an overall length of the vacuum tube is adjusted to provide a space for the neutron generator to move from the first position to the second position.

3. The neutron capture therapy system according to claim 2, wherein the overall length of the vacuum tube is decreasable in an irradiation direction of the neutron beam to provide a space for the neutron generator to move outside the accommodating portion in the irradiation direction of the neutron beam.

4. The neutron capture therapy system according to claim 3, wherein the vacuum tube at least comprises a first vacuum tube portion connected to the accelerator, a second vacuum tube portion accommodated in the accommodating portion for receiving the neutron generator, and a third vacuum tube portion for connecting the first vacuum tube portion and the second vacuum tube portion, wherein the third vacuum tube portion is detachable to decrease the overall length of the vacuum tube to provide the space for the neutron generator to move outside the accommodating portion, and at the second position, the neutron generator moves outside the accommodating portion together with the second vacuum tube portion such that the neutron generator falls off from the beam shaping assembly.

5. The neutron capture therapy system according to claim 1, wherein a filler is filled between a periphery of the vacuum tube and an inner wall of the accommodating portion, and the filler is made of a material configured to absorb neutrons or reflect neutrons.

6. The neutron capture therapy system according to claim 5, further comprising a cooling device located in the accommodating portion and configured to cool the neutron generator, wherein the filler is filled at the periphery of the vacuum tube and the inner wall of the accommodating portion to wrap the cooling device with the filler, and at the second position, the cooling device and the filler fall off from the accommodating portion together with the neutron generator.

7. The neutron capture therapy system according to claim 6, wherein the material of the filler is made of lead alloy or aluminum alloy, wherein when the filler is made of lead alloy, the content of lead in the lead alloy is more than or equal to 85%, and when the filler is made of aluminum alloy, the content of aluminum in the aluminum alloy is more than or equal to 85%.

8. The neutron capture therapy system according to claim 1, further comprising a first shielding portion and a second shielding portion adjacent to the moderator and wrapped around a periphery of the accommodating portion, wherein the second shielding portion moves in a direction away from the vacuum tube with respect to the first shielding portion to provide a space for the neutron generator to move from the first position to the second position.

9. A neutron capture therapy system, comprising:
a neutron generator configured to react with charged particles to generate neutrons, wherein the neutrons form a neutron beam, the neutron beam defines a main axis, and wherein the neutron generator moves between a first position and a second position; and a beam shaping assembly which comprises:
an accommodating portion for providing a vacuum tube;
a moderator adjacent to the neutron generator to moderate the neutrons generated by the neutron generator to an epithermal neutron energy region;
a reflector surrounding the moderator to guide deflected neutrons back to the moderator to increase an intensity of epithermal neutrons;
a thermal neutron absorber adjacent to the moderator; and
a radiation shield and a beam exit disposed in the beam shaping assembly,
wherein the radiation shield is configured to shield leaked neutrons and photons to reduce dosage to normal tissue in a non-irradiation area;
wherein the neutron generator is disposed at an end of the vacuum tube, and wherein a shielding device is adjacent to the beam shaping assembly and is removable from the vacuum tube, and the shielding device shields the neutron generator as the neutron generator moves from the first position to the second position.

10. The neutron capture therapy system according to claim 9, wherein the vacuum tube at least comprises: a first vacuum tube portion connected to an accelerator; a second vacuum tube portion accommodated in the accommodating portion for receiving the neutron generator; and a third vacuum tube portion for connecting the first vacuum tube portion and the second vacuum tube portion, wherein the third vacuum tube portion is detachable from the first vacuum tube portion and the second vacuum tube portion, and when the third vacuum tube portion is detached from the first vacuum tube portion and the second vacuum tube portion, the second vacuum tube portion moves to a position where the neutron generator moves outside the accommodating portion together with the second vacuum tube portion such that the neutron generator falls off from the beam shaping assembly.

11. The neutron capture therapy system according to claim 10, wherein the shielding device has a first opening, a second opening and a third opening, the first opening is adjacent to the first vacuum tube portion, the second opening is adjacent to the second vacuum tube portion, and the third vacuum tube portion passes through the third opening and is accommodated in the shielding device.

12. The neutron capture therapy system according to claim 11, wherein when the neutron generator is at the first position, the shielding device is between the first vacuum tube portion and the second vacuum tube portion, the third vacuum tube portion is in the shielding device, the first opening is adjacent to the first vacuum tube portion, and the second opening is adjacent to the second vacuum tube portion; wherein when the third vacuum tube portion is detached from the first vacuum tube portion and the second vacuum tube portion, the neutron generator moves from the first position to the second position, and the neutron generator moves along with the second vacuum tube portion from the accommodating portion of the beam shaping assembly to the shielding device through the second opening.

13. The neutron capture therapy system according to claim 11, wherein the shielding device comprises a bottom wall, and a first side wall and a second side wall connected to the bottom wall, wherein the first side wall and the second side wall are opposite to each other, and wherein the bottom wall, the first side wall and the second side wall form a U-shaped structure having the first opening, the second opening, and the third opening.

14. The neutron capture therapy system according to claim 13, wherein the shielding device further comprises a top wall opposite to the bottom wall, a third side wall and a fourth side wall connecting the bottom wall and the top wall, wherein the third side wall and the fourth side wall are opposite to each other, wherein the bottom wall, the top wall, and the four side walls form a shielding space, wherein the top wall is rotatable around the second side wall or the fourth side wall in a direction away from the shielding space, and wherein the first side wall and the third side wall are respectively rotatable around the bottom wall in the direction away from the shielding space, to enable the shielding device to form the U-shaped structure.

15. The neutron capture therapy system according to claim 14, wherein when the neutron generator is at the first position, the shielding device is between the first vacuum tube portion and the second vacuum tube portion, and the shielding device is the U-shaped structure; wherein when the neutron generator is at the second position, the neutron generator and the second vacuum tube portion are in the shielding device, and the bottom wall, the top wall, and the four side walls of the shielding device form the shielding space to shield the neutron generator.

16. A neutron capture therapy system, comprising:
a neutron generator configured to react with charged particles to generate neutrons, wherein the neutrons form a neutron beam, the neutron beam defines a main axis, and the neutron generator moves between a first position and a second position;
a vacuum tube connected to an accelerator;
an accommodating device made of a shielding material and located vertically below the vacuum tube; and
a beam shaping assembly which comprises:
an accommodating portion, wherein when the neutron generator moves from the first position to the second position, the neutron generator moves outside the accommodating portion and falls into the accommodating device;
a moderator adjacent to the neutron generator to moderate the neutrons generated by the neutron generator to an epithermal neutron energy region;
a reflector surrounding the moderator to guide deflected neutrons back to the moderator to increase an intensity of epithermal neutrons;
a thermal neutron absorber adjacent to the moderator;
a radiation shield configured to shield leaked neutrons and photons to reduce dosage to normal tissue in a non-irradiation area; and
a beam exit disposed in the beam shaping assembly,
wherein the vacuum tube is provided at the accommodating portion, and the neutron generator is disposed at an end of the vacuum tube.

17. The neutron capture therapy system according to claim 16, further comprising a first shielding portion and a second shielding portion adjacent to the moderator and wrapped around a periphery of the accommodating portion, wherein the second shielding portion is capable of moving in a direction away from the vacuum tube with respect to the first shielding portion to provide a space for the neutron generator to move from the first position to the second position.

18. The neutron capture therapy system according to claim 17, wherein the vacuum tube at least comprises a first vacuum tube portion accommodated in the accommodating portion for receiving the neutron generator and a second vacuum tube portion for connecting the first vacuum tube portion and the accelerator, wherein the first vacuum tube portion is detachable from the second vacuum tube portion, and when the first vacuum tube portion is detached from the second vacuum tube portion and the second shielding portion moves to a position where the first vacuum tube portion falls off the accommodating portion, the neutron generator falls off the beam shaping assembly together with the first vacuum tube portion.

19. The neutron capture therapy system according to claim 16, wherein the accommodating device comprises a bottom portion and four side portions connected to the bottom portion, the bottom portion and the four side portions are connected to form an accommodating space having an opening, two rotating portions covering the opening are disposed at the accommodating device, one end of each of the two rotating portions is connected to any side portion, and an other end of each of the two rotating portions is rotatable towards the accommodating space with respect to the connected side portion.

20. The neutron capture therapy system according to claim 19, wherein when the accommodating device is in a natural state, the two rotating portions cover the accommodating space to form a top portion of the accommodating device; when the accommodating device is under an external force, the rotating portions rotate towards the accommodating space to be accommodated in the accommodating space, and when the external force disappears, the rotating portions restore the natural state.

\* \* \* \* \*